(12) United States Patent
Kimishima

(10) Patent No.: US 9,113,804 B2
(45) Date of Patent: Aug. 25, 2015

(54) COUCH DEVICE AND FUNCTIONAL IMAGE/MORPHOLOGICAL IMAGE DIAGNOSIS APPARATUS

(75) Inventor: Sakae Kimishima, Nasushibara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/110,788

(22) PCT Filed: Aug. 9, 2012

(86) PCT No.: PCT/JP2012/070344
§ 371 (c)(1),
(2), (4) Date: Oct. 9, 2013

(87) PCT Pub. No.: WO2013/027596
PCT Pub. Date: Feb. 28, 2013

(65) Prior Publication Data
US 2014/0033433 A1    Feb. 6, 2014

(30) Foreign Application Priority Data

Aug. 19, 2011 (JP) .................................. 2011-179449

(51) Int. Cl.
*A61B 6/04* (2006.01)
*A61B 5/055* (2006.01)

(52) U.S. Cl.
CPC .................. *A61B 6/0407* (2013.01); *A61B 6/04* (2013.01); *A61B 5/0555* (2013.01); *A61B 6/0457* (2013.01); *A61G 2210/50* (2013.01)

(58) Field of Classification Search
CPC ...... A61B 6/04; A61B 6/0407; A61B 6/0457; A61B 5/0555; A61G 2210/50

USPC ....................................................... 5/600, 601
See application file for complete search history.

(56) References Cited

U.S. PATENT DOCUMENTS

| 4,613,122 A | 9/1986 | Manabe |
| 4,927,127 A | 5/1990 | Lock |

(Continued)

FOREIGN PATENT DOCUMENTS

| CN | 2640449 Y | 9/2004 |
| CN | 101273917 A | 10/2008 |

(Continued)

OTHER PUBLICATIONS

International Search Report Issued Nov. 6, 2012 in PCT/JP12/070344 Filed Aug. 9, 2012.

(Continued)

*Primary Examiner* — Peter M Cuomo
*Assistant Examiner* — Brittany Wilson
(74) *Attorney, Agent, or Firm* — Oblon, McClelland, Maier & Neustadt, L.L.P.

(57) ABSTRACT

A couch device including sliders axially supported by lower ends of both of link members, and including nut members. Guide rails substantially horizontally guide each slider. A screw member is arranged along the guide rail and is configured to apply a driving force to each slider when it is relatively rotated for each nut member and, due to the driving force, substantially horizontally transfer each slider. A clutch unit selectively carries out the operations of rotating one nut member integrated with the screw member such that the driving force is prevented from being applied to one slider, or relatively rotating one nut member for the screw member such that the driving force is applied to one slider. A binding unit binds one slider to the guide rail when the driving force is not applied to the one slider.

12 Claims, 8 Drawing Sheets

(56) References Cited

U.S. PATENT DOCUMENTS

| | | | |
|---|---|---|---|
| 6,637,056 B1 | 10/2003 | Tybinkowski et al. | |
| 7,532,922 B2 * | 5/2009 | Smith et al. | 5/601 |
| 7,827,635 B2 * | 11/2010 | Wang et al. | 5/601 |
| 8,126,537 B2 * | 2/2012 | Yakubovsky et al. | 5/601 |
| 8,242,465 B2 * | 8/2012 | Iwata | 5/601 |
| 2006/0167356 A1 * | 7/2006 | Everett et al. | 600/407 |
| 2008/0028526 A1 * | 2/2008 | Kato | 5/601 |
| 2008/0086816 A1 * | 4/2008 | Farooqui | 5/601 |
| 2008/0235873 A1 | 10/2008 | Farooqui | |
| 2011/0092792 A1 * | 4/2011 | Birman | 600/407 |
| 2011/0107515 A1 * | 5/2011 | Brunker et al. | 5/601 |
| 2012/0023671 A1 * | 2/2012 | Miyano et al. | 5/601 |
| 2012/0324648 A1 * | 12/2012 | Amano | 5/601 |

FOREIGN PATENT DOCUMENTS

| | | |
|---|---|---|
| CN | 101496721 A | 8/2009 |
| JP | 64 70052 | 3/1989 |
| JP | 5 305111 | 11/1993 |
| JP | 2001 128966 | 5/2001 |
| JP | 2008 237911 | 10/2008 |
| JP | 2010 46466 | 3/2010 |
| JP | 2011 72327 | 4/2011 |

OTHER PUBLICATIONS

Office Action issued Mar. 10, 2015 in Chinese Patent Application No. 201280025609.3.

* cited by examiner

COUCH DEVICE AND FUNCTIONAL IMAGE/MORPHOLOGICAL IMAGE DIAGNOSIS APPARATUS

TECHNICAL FIELD

The embodiments of the present invention relate to a couch device and a functional image/morphological image diagnosis apparatus.

BACKGROUND ART

Image diagnoses can be mainly classified into morphological image data for observing changes in form and functional image data for observing changes in function. Morphological image diagnosis apparatuses for acquiring morphological image data include an X-ray diagnosis apparatus, an X-ray CT (Computed Tomography) system, an MRI (Magnetic Resonance Imaging) apparatus, and the like, while functional image diagnosis apparatuses for acquiring functional image data include a nuclear medicine diagnosis apparatus such as a PET (Positron Emission Tomography) apparatus and a SPECT (Single Photon Emission CT) apparatus.

The PET apparatus administers medical agents to a subject, the medical agents being labeled by a radio active isotope that discharges a positron. These medical agents are accumulated in an affected part such as a tumor of the subject, and the PET apparatus detects radiations generated when the positron discharged from the inside of a subject disappears. The affected part such as a tumor appears in PET image data acquired by this imaging. When the affected part of the subject is treated by the PET image data, the anatomical position information is not satisfied by the PET image data.

Therefore, recently, in order to acquire morphological image data and functional image data, a functional image/morphological image diagnosis apparatus, in which a morphological image diagnosis apparatus is combined with a functional image diagnosis apparatus, has been developed. For example, a PET-CT apparatus exists in which a PET apparatus is combined with an X-ray CT system (Patent Document 1.)

For example, the PET-CT apparatus has a gantry, a couch, a top, a couch horizontal transferring unit, a top horizontal transferring unit, and a top vertical transferring unit. The gantry has an aperture. A PET imaging position is displaced on the back side of the aperture, while a CT imaging position is displaced on the front side of the aperture.

The couch supports the top. The top is used for mounting the subject thereon. The couch horizontal transferring unit substantially horizontally transfers the couch. The top horizontal transferring unit substantially horizontally transfers the top to the couch. The top vertical transferring unit vertically transfers the top to the couch.

The substantially horizontal transfer of the couch with the couch horizontal transferring unit makes it possible to transfer the subject on the top to the CT imaging position and the PET imaging position. Thus, since the couch is entirely transferred upon imaging, deflections of the top become equivalent upon CT imaging and upon PET imaging.

PRIOR ART DOCUMENT

Patent Document

[Patent Document 1] Japanese Unexamined Patent Application Publication No. 2011-072327

SUMMARY OF THE INVENTION

Problems to be Solved by the Invention

However, according to the above-described example of the PET-CT apparatus, since the couch horizontal transferring unit and the top vertical transferring unit are separately structured, the structure of apparatus is complicated, which is problematic in that the complicated structure becomes factors with regard to the large size and high cost of the apparatus.

The embodiments are intended to solve the above-described problem, with the object of providing a couch device and a functional image/morphological image diagnosis apparatus, which are able to eliminate the factors such as large size and high cost by preventing their structures from being complicated.

Means of Solving the Problems

In order to solve the above-described problems, the couch device of the embodiments comprises a couch, an X link, sliders, guide rails, a screw member, a clutch unit, and a binding unit. The X link is formed of a long shape, and includes two link members arranged in an X-shape, wherein the couch supported by the upper ends of both link members is raised by narrowing the space between the lower ends of both link members and lowered by widening the space between the lower ends. Sliders are axially supported by the lower ends of both link members, and include nut members. Guide rails substantially horizontally guide each slider. A screw member is arranged along the guide rail, is threadably mounted on each nut member, and applies a driving force to each slider when the screw member is relatively rotated for each nut member, and, due to the driving force, substantially horizontally transfers each slider. A clutch unit selectively carries out the following operations, namely, rotating one nut member integrated with the screw member such that the driving force is prevented from being applied to one slider, or relatively rotating one nut member for the screw member such that the driving force is applied to the one slider. A binding unit binds one slider to the guide rails when the driving force is not applied to the one slider, and releases one slider from the guide rails when the driving force is applied to the one slider.

MODES FOR CARRYING OUT THE INVENTION

First Embodiment

A first embodiment of a couch device will be described with reference to FIG. 1 to FIG. 7. The description will be provided assuming that the couch device is used for a PET-CT apparatus.

Figure 1:
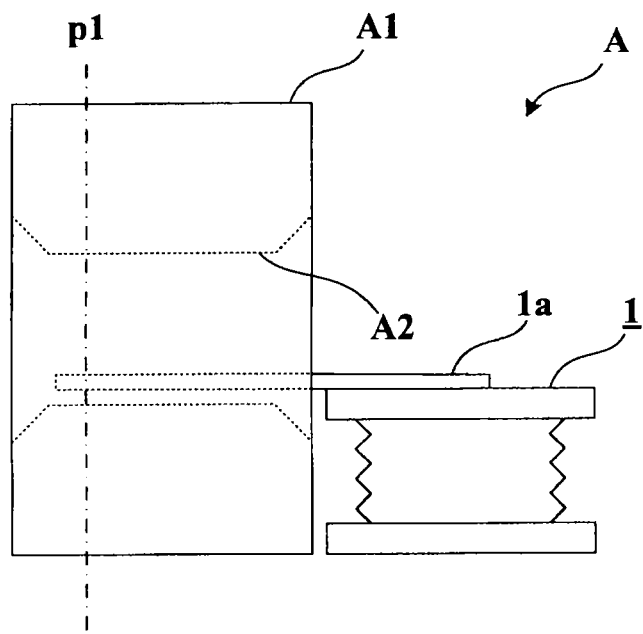
FIG. 1 is a pattern diagram of a couch device transferred to a PET imaging position p1 according to a first embodiment.
Figure 2:
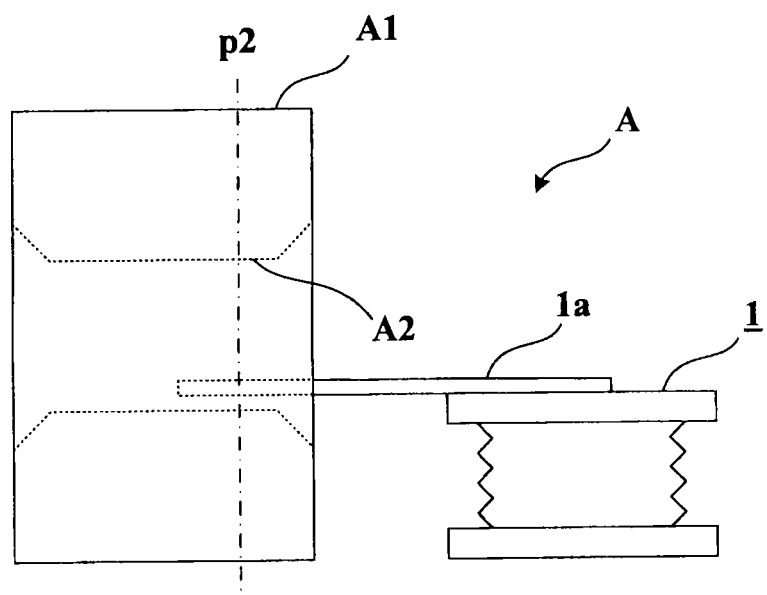
FIG. 2 is a pattern diagram of the couch device transferred to a CT imaging position p2.

FIG. 1 is a pattern diagram of a couch device transferred to a PET imaging position p1, while FIG. 2 is a pattern diagram of the couch device transferred to a CT imaging position p2.

As shown in FIG. 1 and FIG. 2, this PET-CT apparatus A having an aperture A2 of a gantry A1 substantially horizontally transfers a subject on a top 1a between the PET imaging position p1 on the back side of the aperture A2 and the CT imaging position p2 on the front side of the aperture A2, and vertically adjusts the position of the top 1a at respective positions p1 and p2. It is possible for the PET imaging position P1 shown in FIG. 1 to minimize the deflections of the top 1a by transferring the couch near the gantry A1 as much as possible. In addition, it is possible for the CT imaging position p2 shown in FIG. 2 to have a wide space for the gantry A1 and the couch to be capable of easily mounting or lowering a patient onto or from the couch. Since the couch can be vertically transferred at any position, the patient can be mounted or lowered onto or from the couch at any position.

Figure 3:
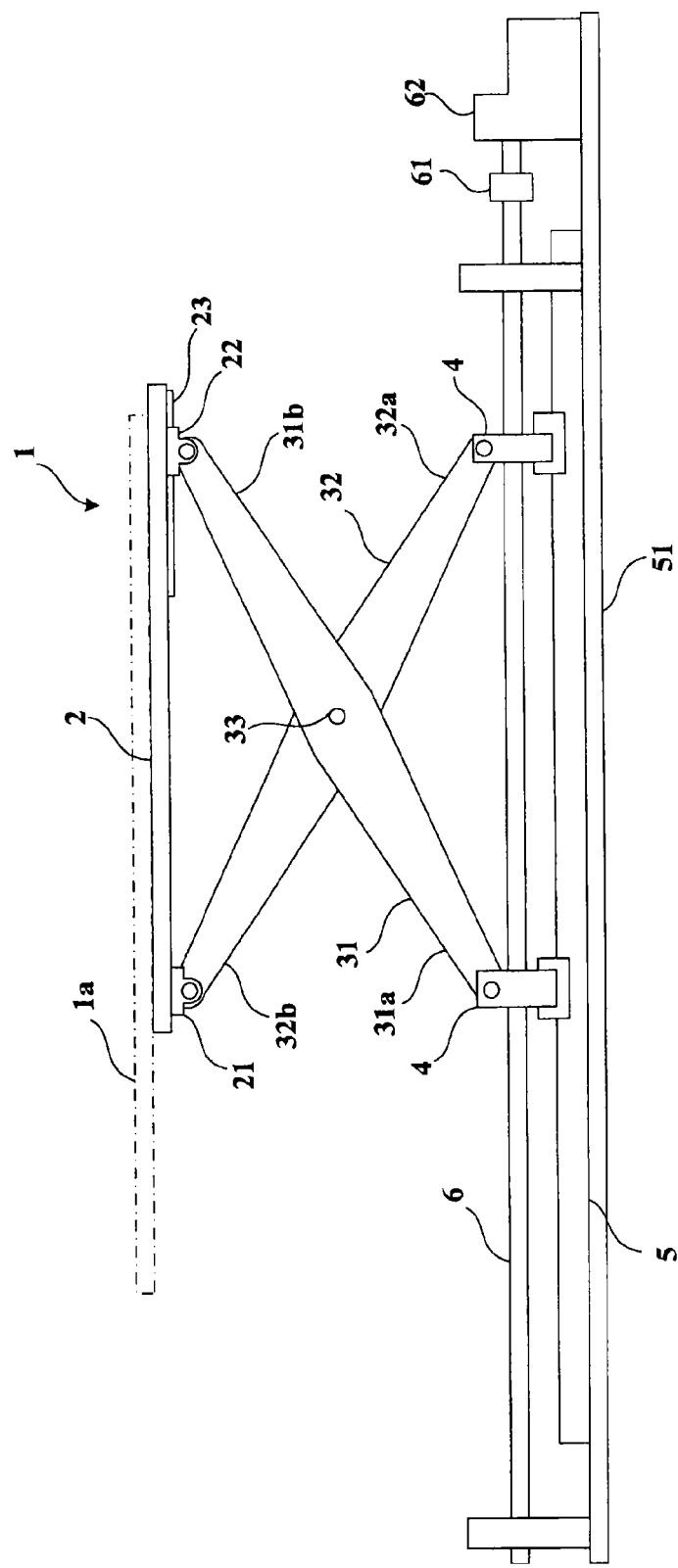
FIG. 3 is a pattern diagram when the couch device is viewed from the front.
Figure 4:
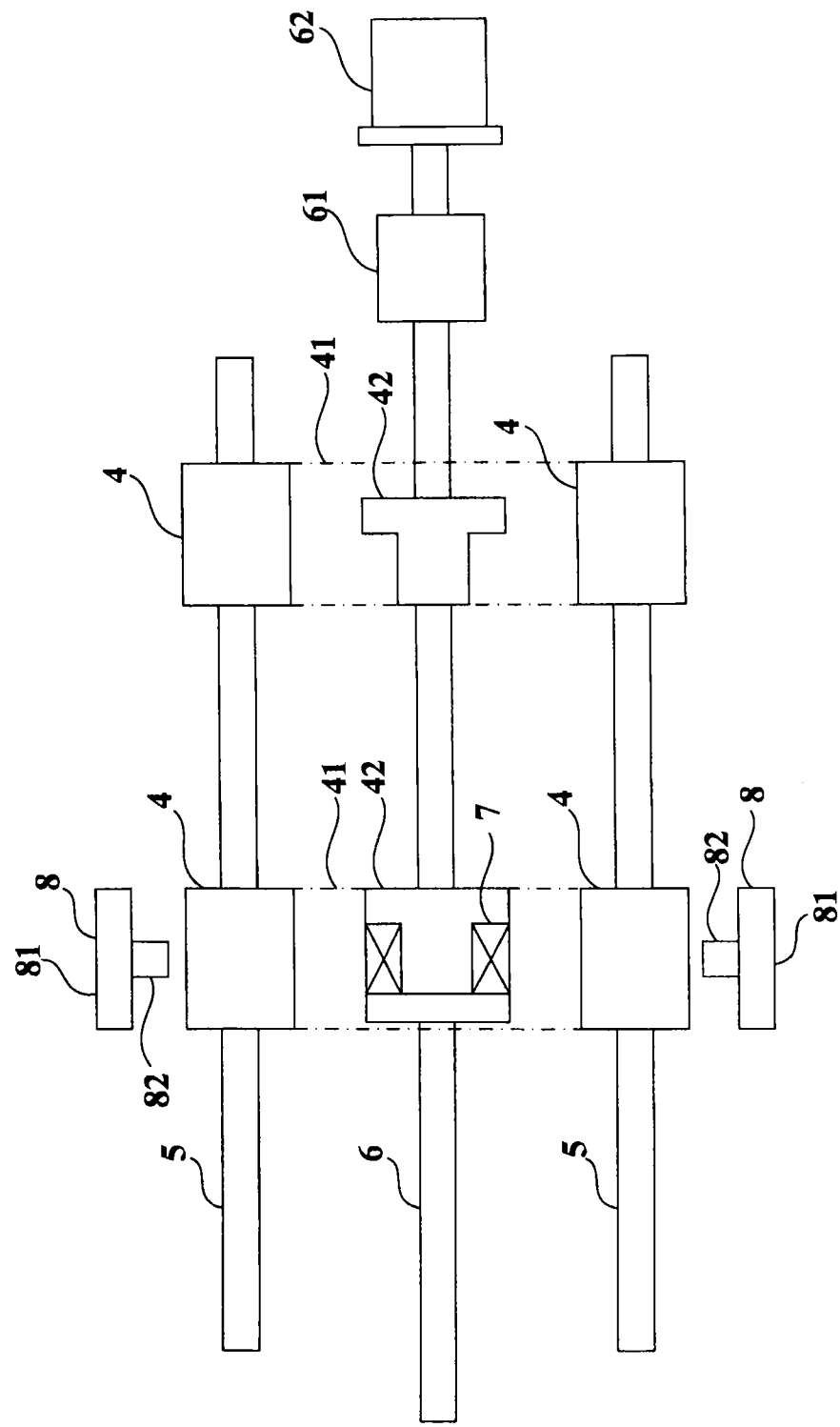
FIG. 4 is a pattern diagram when the couch device is viewed from above.

FIG. 3 is a pattern diagram when the couch device is viewed from the front, while FIG. 4 is a pattern diagram when the couch device is viewed from above. Further, the back side and the front side of the aperture A2 of the gantry A1 correspond to the left side and the right side in FIG. 3, respectively.

As shown in FIG. 3, a couch device 1 has a couch base plate 2, an X link 3, sliders 4, guide rails 5, a screw member 6, a clutch unit 7, and binding units 8.

(Couch)

A couch has a couch base plate 2 as a base. Similar to conventional PET-CT apparatuses, supports the top 1a is supported by the base plate 2 such that the top 1a can be substantially horizontally transferred. In the following description, the couch base plate 2 may be referred to as a couch.

A hinge 21 is fixed at the front end of the couch base plate 2. A hinge 22 is arranged at the rear end of the couch base plate 2 such that the hinge 22 can be substantially horizontally transferred (horizontally in FIG. 3) by a guide member 23.

(X Link)

An X link 3 is formed of a long shape, and is provided with two link members 31, 32 arranged in an X-shape.

The center parts of two link members 31, 32 are axially supported with each other by a connecting pin 33.

Further, the lower end 31a of the link member 31 is axially supported by a back-side slider 4 arranged at the back side position (the left side in FIG. 3), while an upper end 31b of the link member 31 is axially supported by the hinge 22.

Further, a lower end 32a of the link member 32 is axially supported by a front-side slider 4 arranged at the front side position (the right side in FIG. 3), while an upper end 32b of the link member 32 is axially supported by the hinge 21.

Figure 7:
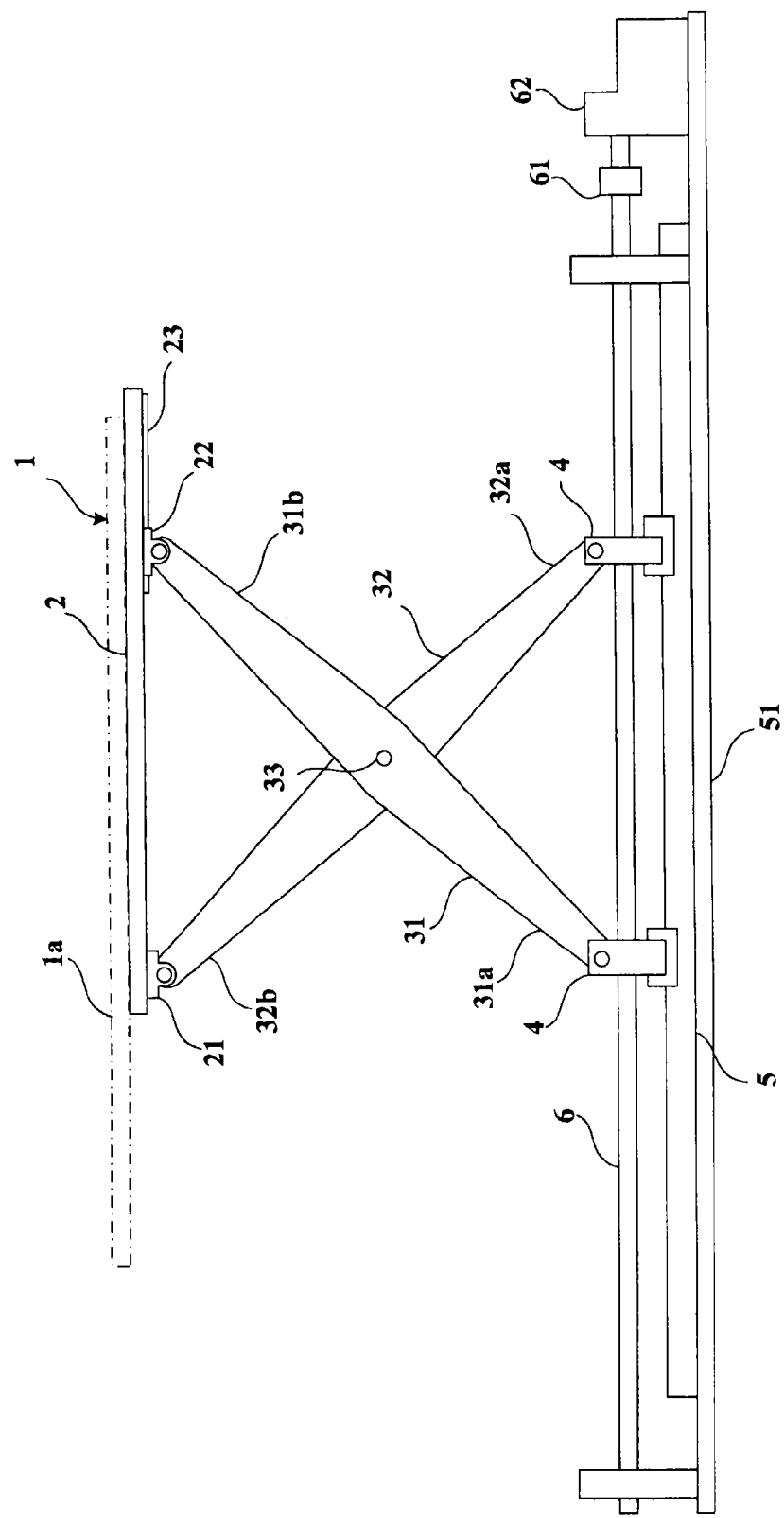
FIG. 7 is a pattern diagram of the couch device when a couch is raised.

As described above, the X link 3 is structured such that the couch base plate 2 (couch) supported by the upper ends 31b, 32b of both link members 31, 32 is raised by narrowing the space between the lower ends 31a, 32a of both link members 31, 32, and the couch base plate 2 is lowered by widening the space between the lower ends 31a, 32a thereof. The lowered couch base plate 2 is shown in FIG. 3, while the raised couch base plate 2 is shown in FIG. 7.

(Slider)

Figure 5A:
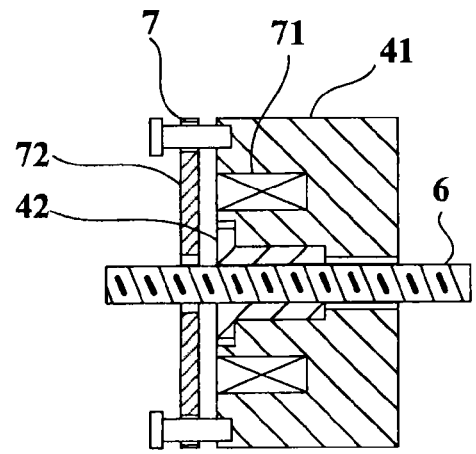
FIG. 5A is a sectional view of a slider when a clutch plate is transferred to a release position.

The sliders 4 on the back side and the front side will be described with reference to FIG. 5A, FIG. 5B, and FIG. 6. FIG. 5A is a sectional view of the slider 4 when the clutch plate is transferred to a release position, FIG. 5B is a sectional view of the slider 4 when the clutch plate is transferred to a fixed position, and FIG. 6 is a sectional view of the slider 4 on the front side in which the nut member is fixed.

Figure 5B:
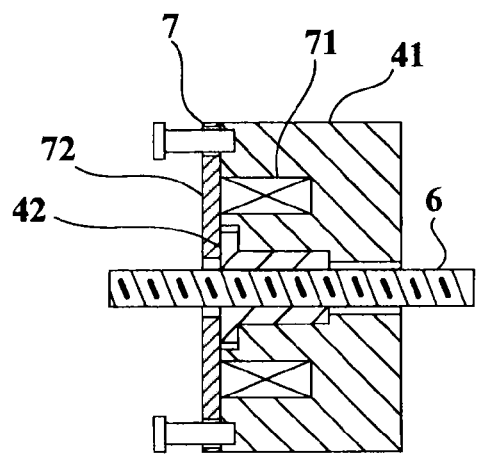
FIG. 5B is a sectional view of the slider when the clutch plate is transferred to a fixed position.

As shown in FIG. 4, FIG. 5A, and FIG. 5B, the slider 4 on the back side has a block 41, a nut member 42, and a clutch unit 7.

The nut member 42 is supported by the block 41 via the clutch unit 7. The clutch unit 7 will be described later.

Figure 6:
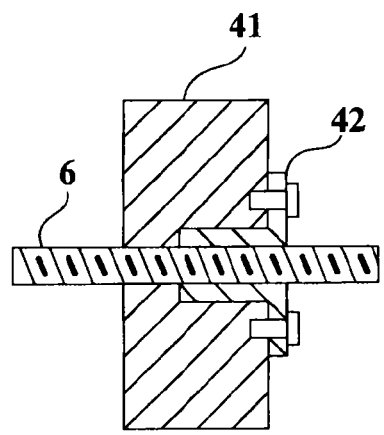
FIG. 6 is a sectional view of the slider when a nut member is fixed.

As shown in FIG. 4 and FIG. 6, the slider 4 on the front side includes the block 41 and the nut member 42. The nut member 42 is fixed to the slider 4 (block 41) on the front side.

(Guide Rail)

As shown in FIG. 3 and FIG. 4, the guide rails 5 substantially horizontally guide the sliders 4 on the back side and the front side. The guide rails 5 are fixed on an installation surface (not shown) via a base member 51. Hereinafter, one of a pair of guide rails 5 and the slider 4 to be guided thereby will be described. This also applies to the other of the pair thereof and the slider 4 to be guided thereby, so the explanation thereof is herein omitted.

(Screw Member)

As shown in FIG. 3 and FIG. 4, the screw member 6 is arranged in a gap between a pair of guide rails 5 along these, and is threadably mounted on each of the nut members 42 of the sliders 4 on the back side and the front side. When the screw member 6 is relatively rotated for respective nut members 42, the screw member 6 applies a driving force to the sliders 4 on the back side and the front side, due to the driving force, substantially horizontally transfers the sliders 4.

One end of the screw member 6 is connected to a driving motor 62 via a deceleration mechanism 61. It is preferable that the screw member 6 comprise a ball screw.

The screw member 6 is configured as follows: when the screw member 6 is normally rotated due to the power of the driving motor 61, for example, and the driving force is applied to the sliders 4 on the back side and the front side, the sliders 4 on the back side and the front side are transferred in one substantially horizontal direction (the left direction in FIG. 3 and FIG. 4), and when the screw member 6 is reversely rotated and the driving force is applied to the sliders 4 on the back side and the front side, the sliders 4 on the back side and the front side are transferred in the other substantially horizontal direction (the right direction in FIG. 3 and FIG. 4.)

(Clutch Unit)

As shown in FIG. 4, FIG. 5A, and FIG. 5B, the clutch unit 7 is provided on the block 41 of one slider 4 on the back side. The clutch unit 7 includes various publicly known means. For example, the clutch unit 7 has an electromagnet 71 and a clutch plate 72. A power source is electrically connected to the electromagnet 71 via a switch unit. Upon receiving attractive and repulsive forces caused by the electromagnet 71, the clutch plate 72 reciprocates between a first position (the release position shown in FIG. 5A) and a second position (the fixed position shown in FIG. 5B). The nut member 42 is released from the slider 4 (block 41) on the back side by means of the clutch plate 72 being transferred to the first position. The nut member 42 is fixed to the slider 4 (block 41) on the back side by means of the clutch plate 72 being transferred to the second position. FIG. 4 shows the simplified clutch unit 7.

The clutch unit 7 is configured to selectively carry out the following operations. The clutch unit 7 rotates the nut member 42 integrated with the screw member 6 by transferring the clutch plate 72 to the first position such that the driving force of the screw member 6 is prevented from being applied to the slider 4 on the back side, and fixing or releasing the nut member 42 for or to the slider 4 on the back side (block 41). Alternatively, the clutch unit 7 relatively transfers the nut member 42 to the screw member 6 by transferring the clutch plate 72 to the second position such that the driving force of the screw member 6 is applied to the slider 4 on the back side, and fixing the nut member 42 to the slider 4 (block 41) on the back side.

[Modified Example of the Clutch Unit]

The clutch unit 7 having the electromagnet 71 and the clutch plate 72 is illustrated; however, not limited to this, the following is also available.

Figure 10:
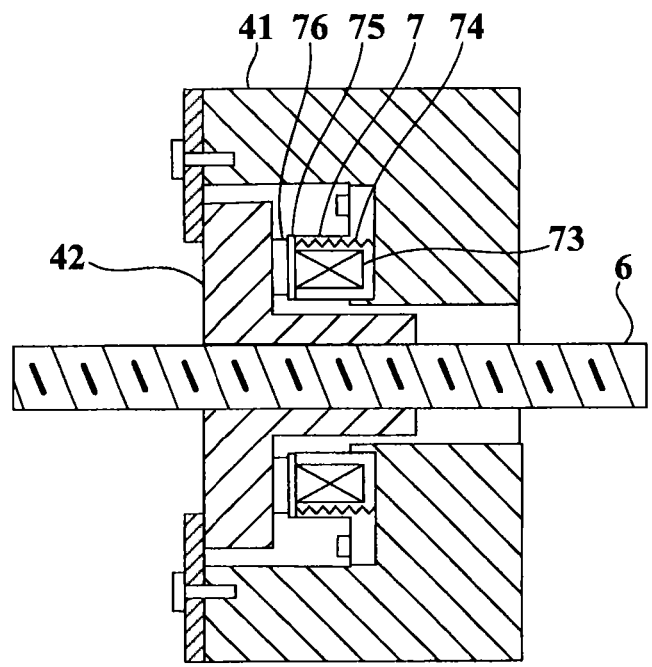
FIG. 10 is a sectional view of a clutch unit according to a modified example.

FIG. 10 is a sectional view of a clutch unit 7 according to a modified example. The clutch unit 7 shown in FIG. 10 is an electromagnetic brake having a coil 73, a spring 74, an armature 75, and a brake lining 76. According to the operation of this electromagnetic brake, braking force is released when the armature 75 is suctioned by the coil 73 and space is generated between the armature 75 and the brake lining 76. Thereby, the nut member 42 is released onto or from the slider 4 on the back side, allowing the nut member 42 to be rotatably integrated with the screw member 6.

On the other hand, braking force is generated when the armature 75 is pressed against the brake lining 76 by the force of the spring 74. Thereby, the nut member 42 is fixed to the slider 4 on the back side, allowing the nut member 42 to be relatively transferred to the screw member 6.

Moreover, with this electromagnetic brake, it is needless to say that, similar to the above-described clutch unit 7 having the electromagnet 71 and the clutch plate 72, the clutch unit 7 is configured to selectively carry out rotation of the nut member 42 integrated with the screw member 6, and relative transferring of the nut member 42 to the screw member 6.

(Binding Unit)

Binding units 8 are provided on the side of the guide rails 5. Here, the side of the guide rails 5 includes the guide rails 5 and the place to which the guide rails 5 are fixed (for example, the base member 51). The binding units 8 are provided at positions corresponding to the sliders 4 on the back side when the sliders 4 are transferred to the backmost position and the frontmost position (in the couch, the PET imaging position p1 and the CT imaging position p2), respectively.

In addition, FIG. 3 and FIG. 4 only show the binding unit 8 provided at the position corresponding to the slider 4 on the back side when the slider 4 is transferred to the backmost position, and the binding unit 8 provided at the position corresponding to the slider 4 on the back side when the slider 4 is transferred to the frontmost position is omitted.

Further, the binding units 8 are provided to each of a pair of the guide rail 5 sides; however, both binding units 8 are of the same structure. Therefore, only one binding unit 8 is described and the description of other binding unit 8 is omitted herein.

When the driving force of the screw member 6 is not applied to the slider 4 on the back side, the binding unit 8 binds the slider 4 on the back side to the guide rail 5, and when this driving force is applied to the slider 4 on the back side, the binding unit 8 releases the slider 4 on the back side from the guide rail 5.

An example of the binding unit 8 includes a solenoid. The solenoid comprises a body 81, a coil (not shown), and a shaft 82. The solenoid is configured such that the shaft 82 is exposed from the body 81 when an electric current passes through the coil. The coil is electrically connected to a power source (not shown) via a switch unit (not shown).

The solenoid transfers the sliders 4 on the back side between the position at which the slider 4 on the back side is bound to the guide rail 5 by fastening the shaft 82 to a fastened part (not shown) of the slider 4 on the back side and the position at which the slider 4 on the back side is released from the guide rail 5 by releasing the shaft 82 from the slider 4 on the back side.

According to an example of the binding unit 8, it is possible to bind the slider 4 on the back side at the backmost position.

[Operation of the Couch Device]

Next, the operation of the couch device when the position of the couch (couch base plate 2) is horizontally and vertically adjusted will be described with reference to FIG. 3 and FIG. 7. FIG. 7 is a pattern diagram of the couch device when the couch is raised. In FIG. 3 and FIG. 7, an explanation will be provided assuming that the couch is located at the PET imaging position p1 (the back side of the aperture of the gantry).

The positional adjustment of the couch is carried out with the cooperation between the clutch unit 7 and the binding unit 8. The positional adjustment of the couch described below is carried out when the operator turns on or off switch units of the clutch unit 7 and the binding unit 8.

(Transfer of the Couch to the Back Side)

When the couch is transferred from the CT imaging position p2 to the PET imaging position p1 (the back side), the clutch unit 7 relatively transfers the nut member 42 for the screw member 6 such that the driving force of the screw member 6 is applied to the slider 4 on the back side. In this case, the binding unit 8 releases the slider 4 on the back side from the guide rail 5.

Thereby, the sliders 4 on the back side and the front side are transferred to the back side along the guide rails 5 by the applied driving force. In this case, the couch is also transferred to the back side. FIG. 3 shows the couch base plate 2 transferred to the PET imaging position p1. In this case, the slider 4 on the back side is transferred to the backmost position within a transferable range.

(Raising the Couch)

When the couch is transferred to the PET imaging position p1, the clutch unit 7 rotates the nut member 42 integrated with the screw member 6 such that the driving force of the screw member 6 is not applied to the slider 4 on the back side. In this case, the binding unit 8 binds the slider 4 on the back side to the guide rail 5.

Thereby, the slider 4 on the back side is bound at the backmost position, while the slider 4 on the front side is only transferred to the back side. As a result, the space between the lower ends 31*a*, 32*a* of both link members 31, 32 is narrowed, raising the couch supported by the upper ends 31*b*, 32*b* of both link members 31, 32. The raised couch is shown in FIG. 7. Further, the top 1*a* with the subject mounted thereon is also raised.

When the couch reaches a specific height, the rotation of the screw member 6 is stopped. In this case, due to the binding unit 8 and the screw member 6, front-back transfer of the lower ends 31*a*, 32*a* of both link members 31, 32 is prevented, making it possible to maintain the couch at the specific height. Thereby, it is possible to adjust the height of the couch in accordance with the rotational amount of the screw member 6.

(Lowering the Couch)

In order to lower the couch, it is simply necessary to rotate the screw member 6 in reverse. Thereby, the slider 4 on the back side is bound at the backmost position, while the slider 4 on the front side is only transferred to the front side (the right direction in FIG. 3 and FIG. 4.) As a result, the space between the lower ends 31a, 32a of both link members 31, 32 is widened, lowering the couch supported by the upper ends 31b, 32b of both link members 31, 32. Further, the top 1a having the subject mounted thereon is also lowered.

When the couch reaches a specific height, the rotation of the screw member 6 is stopped. In this case, due to the binding unit 8 and the screw member 6, front-back transfer of the lower ends 31a, 32a of both link members 31, 32 is prevented, making it possible to maintain the couch at the specific height.
(Transfer of the Couch to the Front Side)

In order to transfer the couch from the PET imaging position p1 to the CT imaging position p2 (the front side: the right direction in FIG. 3 and FIG. 4), it is simply necessary to rotate the screw member 6 in reverse. The clutch unit 7 relatively rotates the nut member 42 for the screw member 6 such that the driving force of the screw member 6 is applied to the slider 4 on the back side. In this case, the binding unit 8 releases the slider 4 on the back side from the guide rail 5.

Thereby, the driving force is applied to the sliders 4 on the back side and the front side, the sliders 4 transferring to the front side along the guide rails 5. In this case, the couch is also transferred to the front side. Transfer of the couch to the CT imaging position p2 and the height adjustment of the couch at the CT imaging position p2 are carried out similar to the example of the PET imaging position p1.

As described above, it is possible to transfer the couch to a specific position in the horizontal and vertical directions, and maintain the couch at the specific position with the cooperation between the clutch unit 7 and the binding unit 8.

The couch horizontal transferring unit and the top vertical transferring unit are separately configured according to the example of conventional PET-CT apparatuses.

In contrast, in the PET-CT apparatus according to the embodiment, a means of substantially horizontally transferring the couch (a couch horizontal transferring unit) and a means of raising and lowering the couch (a top vertical transferring unit) are configured by a single mechanism, thereby it is possible to prevent complicating the configuration.

In this embodiment, a structure in which the binding unit 8 binds the slider 4 on the back side to the side of the guide rail 5 is described; however, a structure in which the binding unit 8 binds the slider 4 on the front side to the side of the guide rail 5 is also possible.

With such a structure, for example, the transfer of the couch located at the CT imaging position p2 is adjusted as follows.

The clutch unit 7 relatively rotates the nut member 42 of the slider 4 on the front side for the screw member 6 such that the driving force of the screw member 6 is applied to the slider 4 on the front side. When the screw member is rotated normally, the sliders 4 on the front side and the back side are concurrently transferred to the back side, thereby transferring the couch from the CT imaging position p2 to the PET imaging position p1. In this case, the binding unit 8 binds the slider 4 on the front side to the side of the guide rail 5. In addition, the clutch unit 7 rotates the nut member 42 of the slider 4 on the front side integrated with the screw member 6 such that the driving force of the screw member 6 is not applied to the slider 4 on the front side.

Subsequently, when the screw member is rotated in reverse, only the slider 4 on the back side is transferred to the front side to approach the slider 4 on the front side. As a result, the space between the lower ends 31a, 32a of the link members 31, 32 is narrowed, and the couch is raised. In contrast, when the screw member is rotated normally, only the slider 4 on the back side is transferred to the back side to separate from the slider 4 on the front side. As a result, the space between the lower ends 31a, 32a of the link members 31, 32 is widened, and the couch is lowered. In this way, height adjustment and positional adjustment of the couch can be carried out.

[Modified Example of the Binding Unit]

According to the above example of the binding unit 8, the binding unit 8 is provided on the side of the guide rail 5; however, according to a modified example of the binding unit, the binding unit 8 may be provided on the side of the slider 4 on the back side. Here, the side of the slider 4 on the back side includes the slider 4 on the back side and a member that is integrally transferred with this slider 4 (for example, the lower end 31a of the link member 31).

As the binding unit 8, a solenoid is provided similar to the above example of the binding unit 8. In other words, the solenoid transfers the slider 4 on the back side between the position at which the slider 4 on the back side is bound to the guide rail 5 by fastening the shaft 82 to a fastened part (not shown) of the guide rail 5 and the position at which the slider 4 on the back side is released from the guide rail 5 by releasing the shaft 82 from the guide rail 5.

According to the modified example of the binding unit 8, it is possible to bind the slider 4 on the back side for each specific space by providing the fastened part (for example, a concave part) to the guide rail 5 for each specific space (for example, 2 cm). Further, it is possible to carry out height position adjustment of the couch at the position where the slider 4 on the back side is bound.

Second Embodiment

Figure 8:
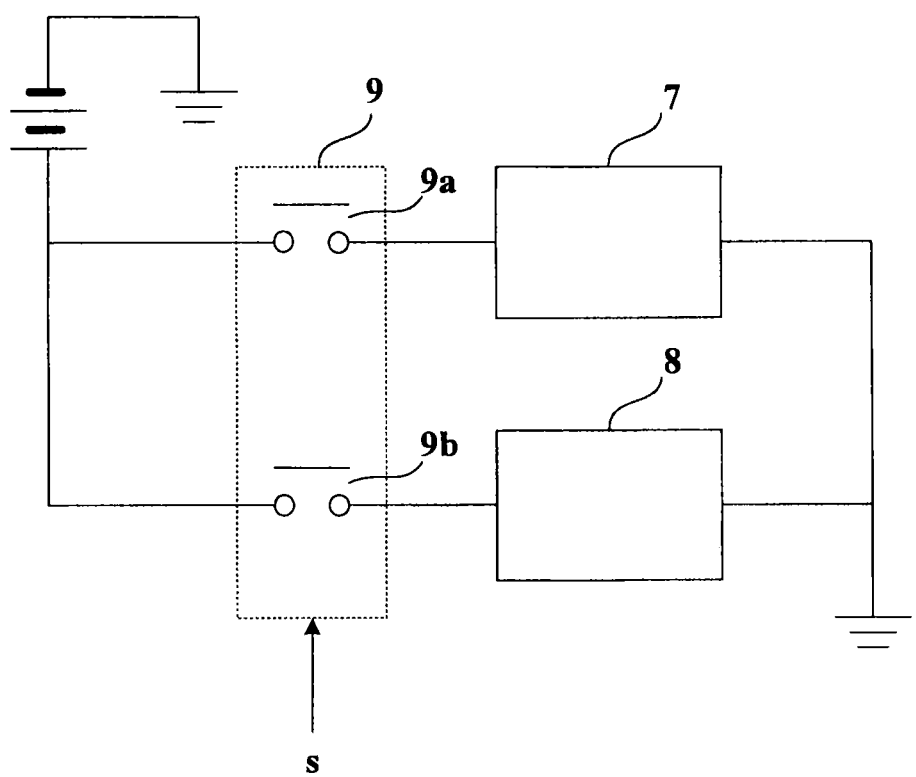
FIG. 8 is a circuit diagram showing an example of a control unit according to a second embodiment.

Next, a couch device according to a second embodiment will be described with reference to FIG. 8.

In the second embodiment, components similar in structure with the first embodiment are given identical numbers and the explanations thereof are omitted herein.

In the first embodiment, the operator operates each switch unit of the clutch unit 7 and the binding unit 8, allowing the clutch unit 7 to cooperate with the binding unit 8. Thereby, the transfer of the couch is adjusted to a specific position in the horizontal and vertical directions.
(Control Unit)

In the second embodiment, a control unit 9 is provided for allowing the clutch unit 7 to cooperate with the binding unit 8.

The control unit 9 has switches 9a, 9b as a contact a. A power source is electrically connected to the clutch unit 7 and the binding unit 8 via the switches 9a, 9b.

Upon receiving instructions to substantially horizontally transfer the couch (denoted by s in FIG. 8), the control unit 9 turns on the switches 9a, 9b. The clutch unit 7 then allows the nut member 42 to be relatively rotated for the screw member 6 such that the driving force of the screw member 6 is applied to the slider 4 on the back side. In addition, the binding unit 8 releases the slider 4 on the back side from the guide rail 5.

Upon receiving instructions a to vertically transfer the couch, the control unit 9 turns off the switches 9a, 9b. The clutch unit 7 then allows the nut member 42 to be integrally rotated with the screw member 6 such that the driving force of the screw member 6 is not applied to the slider 4 on the back side. In addition, the binding unit 8 binds the slider 4 on the back side to the guide rail 5.

In this embodiment, simply by having the operator instruct to which position the couch is to be transferred, the control unit 9 receives the instructions, and controls the clutch unit 7 and the binding unit 8 so as to carry out the cooperation therebetween. Thus, the operation for the positional adjustment of the couch is simplified.

Third Embodiment

Next, a couch device in a third embodiment will be described with reference to FIG. 9.

In the third embodiment, components similar in structure with the first embodiment are given identical numbers and the explanations thereof are omitted herein.

In the first embodiment, the binding unit 8 is a solenoid; however, in this third embodiment, the binding unit 8 comprises a rack 85, gears 86, and brakes 88.

(Rack)

Figure 9:
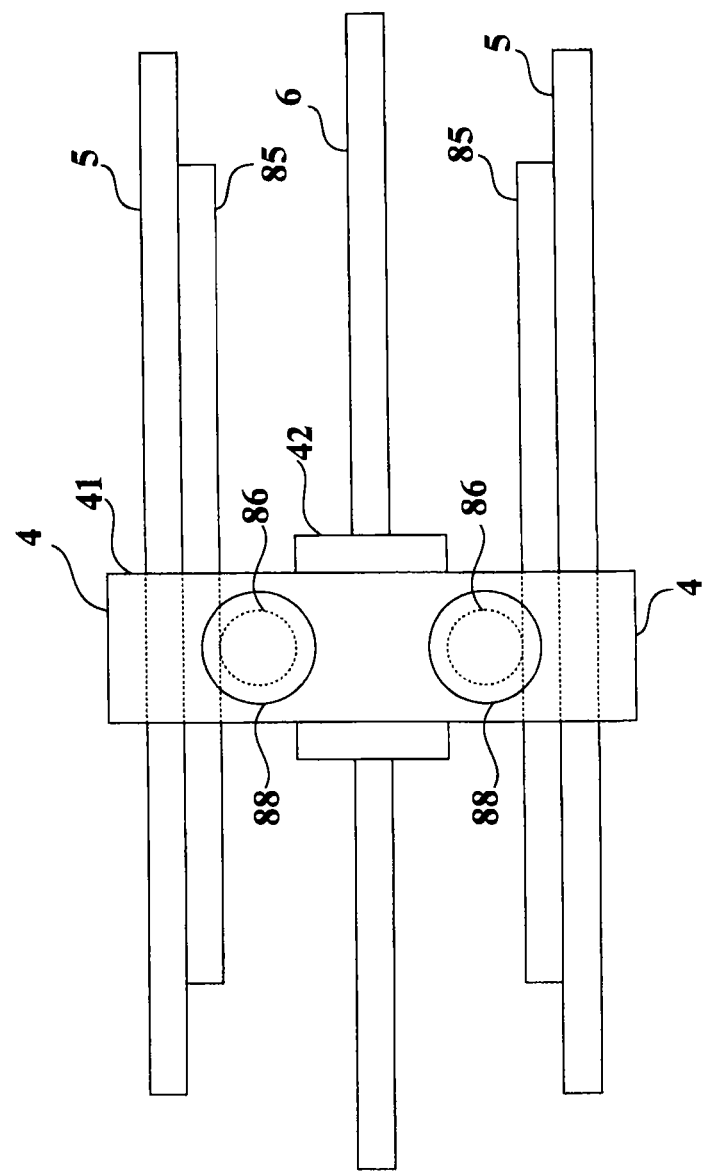
FIG. 9 is a pattern diagram when a slider, and the like according to a third embodiment are viewed from above.

FIG. 9 is a pattern diagram when the slider 4, and the like. are viewed from above. As shown in FIG. 9, the rack 85 is arranged along the guide rail 5.

(Gear)

The gear 86 is provided on the slider 4 on the back side, rolling on the rack 85 in accordance with the relative transfer of the slider 4 on the back side for the guide rail 5.

(Brake Unit)

The brake unit 88 stops the relative transfer of the slider 4 on the back side for the guide rail 5 by stopping rolling of the gear 86.

It is possible to bind the slider 4 on the back side such that this slider 4 is not transferred to any position within a transferable range of the slider 4 on the back side. Thereby, it is possible to transfer the couch to any position, and adjust the height of the couch at the position within a transferable range.

In each of the above-described embodiments and modified examples, the binding unit 8 is described; however, as long as the binding unit 8 binds the slider 4 and the side of the guide rail 5 such that they are not relatively transferred, releasing this binding such that they are relatively transferred, various publicly known means can be applied.

(Functional Image/Morphological Image Diagnosis Apparatus)

In the above-described embodiments, the couch device 1 is provided in the PET/CT apparatus; however, not limited to this, the couch device 1 may be provided in a functional image/morphological image diagnosis apparatus configured by comprising a morphological image diagnosis apparatus having a first diagnosis position and configured to acquire morphological image data, along with a functional image diagnosis apparatus having a second diagnosis position and configured to acquire functional image data.

As described above, the morphological image diagnosis apparatus for acquiring morphological image data includes X-ray diagnosis apparatuses, X-ray CT systems, MRI apparatuses, and the like. The functional image diagnosis apparatus for acquiring functional image data includes nuclear medicine diagnosis apparatuses such as PET apparatuses and the SPECT apparatuses.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

EXPLANATION OF SYMBOLS

1 couch device
1*a* top
2 couch base plate
3 X link
4 slider
5 guide rail
6 screw member
7 clutch unit
71 electromagnet
72 clutch plate
8 binding unit
9 control unit
p1 PET imaging position
p2 CT imaging position

The invention claimed is:

1. A couch device comprising:
   a couch;
   an X link of a long shape including two link members arranged in an X-shape, wherein the couch supported by the upper ends of both link members is raised by narrowing the space between the lower ends of both link members and lowered by widening the space between the lower ends thereof;
   sliders axially supported by the lower ends of both link members, including nut members;
   guide rails configured to substantially horizontally guide each slider;
   a screw member arranged along the guide rails and threadably mounted on each nut member, configured to apply a driving force to each slider when the screw member is relatively rotated for each nut member and, due to the driving force, substantially horizontally transfer each slider;
   a clutch unit; and
   a binding unit, wherein
   the binding unit is configured to release one slider from the guide rail to horizontally transfer the couch when the clutch unit rotates one nut member relatively to the screw member such that the driving force is applied to the one slider, and
   the binding unit is configured to bind one slider to the guide rail to vertically transfer the couch when the clutch unit rotates one nut member integrally with the screw member such that the driving force is prevented from being applied to the one slider.

2. The couch device according to claim 1, further comprising a control unit configured to control the clutch unit and the binding unit,
   wherein, upon receiving instructions to substantially horizontally transfer the couch, the control unit is configured to control the binding unit so as to release the one slider from the guide rail, and control the clutch unit so as to relatively rotate the one nut member for the screw member, and
   upon receiving instructions to vertically transfer the couch, the control unit is configured to control the binding unit so as to bind the one slider to the guide rail, and control the clutch unit so as to rotate the one nut member integrated with the screw member.

3. The couch device according to claim 1,
   wherein the binding unit is provided on the side of the guide rail,
   wherein the binding unit comprises a shaft and is configured to transfer the slider between the position where one slider is bound to the guide rail by fastening the shaft to the one slider and the position where one slider is released from the guide rail by releasing the shaft from the one slider.

4. The couch device according to claim 1,
wherein the binding unit is provided on the side of one slider,
wherein the binding unit comprises a shaft and is configured to transfer the shaft between the position where one slider is bound to the guide rail by fastening the shaft to the guide rail and the position where the one slider is released from the guide rail by releasing the shaft from the guide rail.

5. The couch device according to claim 1,
wherein the binding unit comprises:
a rack provided along the guide rail;
a gear provided on one slider, rolling on the rack in accordance with the relative transfer of the one slider for the guide rail; and
a brake unit configured to prevent the relative transfer of the one slider for the guide rail by stopping rolling of the gear.

6. A functional image/morphological image diagnosis apparatus comprising the couch device,
wherein the functional image/morphological image diagnosis apparatus is configured by comprising a morphological image diagnosis apparatus having a first diagnosis position and configured to acquire morphological image data, along with a functional image diagnosis apparatus having a second diagnosis position and configured to acquire functional image data, and wherein, the couch device comprises:
a couch;
an X link of a long shape including two link members arranged in an X-shape, wherein the couch supported by the upper ends of both link members is raised by narrowing the space between the lower ends of both link members and lowered by widening the space between the lower ends thereof;
sliders axially supported by the lower ends of both link members, including nut members;
guide rails configured to substantially horizontally guide each slider;
a screw member arranged along the guide rails and threadably mounted on each nut member, configured to apply a driving force to each slider when the screw member is relatively rotated for each nut member and, due to the driving force, substantially horizontally transfer each slider;
a clutch unit; and
a binding unit, wherein
the binding unit is configured to release one slider from the guide rail to horizontally transfer the couch when the clutch unit rotates one nut member relatively to the screw member such that the driving force is applied to the one slider, and
the binding unit is configured to bind one slider to the guide rail to vertically transfer the couch when the clutch unit rotates one nut member integrally with the screw member such that the driving force is prevented from being applied to the one slider.

7. The functional image/morphological image diagnosis apparatus according to claim 6,
wherein the functional image/morphological image diagnosis apparatus is a PET/CT apparatus configured by comprising a PET apparatus for acquiring functional image data based on the detection information of radiations generated from a subject by applying specific medical agents to the subject, along with a CT system for acquiring morphological image data based on the detection information of X-rays transmitted through the subject.

8. The couch device according to claim 2,
wherein the binding unit is provided on the side of the guide rail,
wherein the binding unit comprises a shaft and is configured to transfer the slider between the position where one slider is bound to the guide rail by fastening the shaft to the one slider and the position where one slider is released from the guide rail by releasing the shaft from the one slider.

9. The couch device according to claim 2,
wherein the binding unit is provided on the side of one slider,
wherein the binding unit comprises a shaft and is configured to transfer the shaft between the position where one slider is bound to the guide rail by fastening the shaft to the guide rail and the position where the one slider is released from the guide rail by releasing the shaft from the guide rail.

10. The couch device according to claim 2,
wherein the binding unit comprises:
a rack provided along the guide rail;
a gear provided on one slider, rolling on the rack in accordance with the relative transfer of the one slider for the guide rail; and
a brake unit configured to prevent the relative transfer of the one slider for the guide rail by stopping rolling of the gear.

11. The functional image/morphological image diagnosis apparatus according to claim 6, further comprising a control unit configured to control the clutch unit and the binding unit,
wherein, upon receiving instructions to substantially horizontally transfer the couch, the control unit is configured to control the binding unit so as to release the one slider from the guide rail, and control the clutch unit so as to relatively rotate the one nut member for the screw member, and
upon receiving instructions to vertically transfer the couch, the control unit is configured to control the binding unit so as to bind the one slider to the guide rail, and control the clutch unit so as to rotate the one nut member integrated with the screw member.

12. The functional image/morphological image diagnosis apparatus according to claim 11,
wherein the functional image/morphological image diagnosis apparatus is a PET/CT apparatus configured by comprising a PET apparatus for acquiring functional image data based on the detection information of radiations generated from a subject by applying specific medical agents to the subject, along with a CT system for acquiring morphological image data based on the detection information of X-rays transmitted through the subject.

* * * * *